(12) United States Patent
Miura

(10) Patent No.: US 8,436,375 B2
(45) Date of Patent: May 7, 2013

(54) LIGHT ILLUMINATING DEVICE

(75) Inventor: Kenji Miura, Kyoto (JP)

(73) Assignee: CCS Inc., Kyoto (JP)

( * ) Notice: Subject to any disclaimer, the term of this patent is extended or adjusted under 35 U.S.C. 154(b) by 160 days.

(21) Appl. No.: 13/054,073

(22) PCT Filed: Jun. 1, 2009

(86) PCT No.: PCT/JP2009/059978
§ 371 (c)(1),
(2), (4) Date: Jan. 13, 2011

(87) PCT Pub. No.: WO2010/007835
PCT Pub. Date: Jan. 21, 2010

(65) Prior Publication Data
US 2011/0114977 A1   May 19, 2011

(30) Foreign Application Priority Data

Jul. 15, 2008   (JP) ................................. 2008-184156

(51) Int. Cl.
*H01L 33/00* (2010.01)
(52) U.S. Cl.
USPC ....... 257/91; 257/678; 257/723; 257/E33.056
(58) Field of Classification Search .................... 257/91, 257/678, 723, E33.056
See application file for complete search history.

(56) References Cited

FOREIGN PATENT DOCUMENTS

| JP | 2005-259653 A | 9/2005 |
|---|---|---|
| JP | 2006-079946 A | 3/2006 |
| JP | 3126166 U | 9/2006 |
| JP | 2006-275790 A | 10/2006 |
| JP | 2007-012311 A | 1/2007 |
| JP | 2007-059073 A | 3/2007 |
| JP | 2007271512 A | 10/2007 |

OTHER PUBLICATIONS

ISA Japanese Patent Office, International Search Report of PCT/JP2009/059978, Jul. 7, 2009, 2 pages.
"Safety Light Curtain," published by OMRON Corporation, Apr. 23, 2011, 13 pages.
"Area Sensors," published by SUNX Co., Ltd., Apr. 23, 2011, 18 pages.
"Photoelectronic Sensor," published by OPTEX FA Co., Ltd., Apr. 23, 2011, 11 pages.
"Photoelectronic Sensor," published by OPTEX FA Co., Ltd., Apr. 23, 2011, 5 pages.

*Primary Examiner* — Long Pham
(74) *Attorney, Agent, or Firm* — Alleman Hall McCoy Russell & Tuttle LLP

(57) ABSTRACT

To reliably keep an LED board and a heat conductive member in close contact to improve the heat-dissipation efficiency and to reliably position an LED and an optical element, such as a lens part, arranged in a housing are a slim LED board, the housing that has an accommodating concave part to house the LED board, a heat conductive member that is arranged between the LED board and the accommodating concave part, a pressing member that has the lens part and that presses a long side edge part of the LED board against a bottom surface of the accommodating concave part of the housing, a securing mechanism for securing the LED board, the heat conductive member and the pressing member to the housing, and a positioning mechanism for positioning the lens part relative to the LED.

4 Claims, 9 Drawing Sheets

LIGHT ILLUMINATING DEVICE

TECHNICAL FIELD

This invention relates to a light illuminating device that can irradiate linear light by the use of multiple LEDs, and more preferably relates to a light illuminating device used for inspection, such as for detecting whether or not there are flaws in a predetermined irradiated area of, especially, a workpiece (a product), or for reading indicia.

BACKGROUND ART

Some light illuminating device such as a linear light illuminating device comprises a lengthy LED board on which multiple LEDs are loaded, a housing that houses the LED board, and a heat conductive member that is arranged between the LED board and the housing and that conducts heat produced by the LED board away to a radiation fin arranged on the housing.

Conventionally, as a method for securing the LED board to the housing, it is known to press both end parts of a longitudinal direction of the LED board toward the housing side through the heat conductive member.

However, in a case that the heat conductive member is made of a material such as silicon rubber or the like having viscoelasticity, with the above-mentioned arrangement, wherein the both end parts of the longitudinal direction of the LED board are pressed so as to secure the LED board, the LED warps and therefore the LED board is prevented from being tightly attached to the heat conductive member. As a result, there are problems in that not only the heat conductive efficiency is decreased, but also each light irradiating direction of the LEDs is misaligned.

In addition, LEDs that are known to be loadable on the LED board are an LED of a bullet-shaped type and an LED of a surface mounting type. In a case that an LED of the surface mounting type is used, as shown in the patent document 1, it is necessary to arrange a lens part member separately from the LED and thus the lens part member is secured to the housing.

However, with this arrangement, it is necessary to secure the LED board and the lens part member respectively to the housing, which requires positioning of the LED and the lens part member. As a result, there is a problem that workability is extremely low.

PATENT DOCUMENT

Patent document 1: Japan patent laid-open number 2005-259653

DISCLOSURE OF THE INVENTION

Problems to be Solved by the Invention

Accordingly, the present invention intends to solve all of these problems, and a main object of this invention is to reliably keep an LED board and a heat conductive member in close contact to improve the heat-dissipation efficiency and to reliably position an LED and an optical element, such as a lens part, arranged in a housing with a simple arrangement having fewer components.

Means to Solve the Problems

More specifically, the light illuminating device in accordance with claim 1 of this invention comprises a lengthy LED board on which multiple LEDs are loaded, a housing that has an accommodating concave part to house the LED board, a heat conductive member that is arranged between a back surface of the LED board and a bottom surface of the accommodating concave part, a pressing member that has multiple lens parts corresponding to each of the multiple LEDs and that presses a long side edge part of the LED board against the bottom surface of the accommodating concave part of the housing, a securing mechanism for securing the LED board, the heat conductive member and the pressing member to the housing, and a positioning mechanism for positioning the multiple lens part relative to the multiple LEDs, and is characterized in that the securing mechanism comprises a first surface that is arranged on either one of the housing and the pressing member and that faces a bottom surface side of the accommodating concave part and a second surface that is arranged on the other of the housing and the pressing member and that makes an abutting contact with the first surface and faces an opening side of the accommodating concave part, the positioning mechanism comprises a convex part that is arranged on either one of the LED board and the pressing member and a concave part that is arranged on the other of the LED board and the pressing member and that fits over the convex part, and each of the multiple lens parts is positioned for each of the multiple LEDs, respectively, by making the first surface of the securing mechanism in abutting contact with the second surface of the securing mechanism and by fittingly inserting the convex part of the positioning mechanism into the concave part of the positioning mechanism in a state that the pressing member presses the long side edge part of the LED board, so that the back surface of the LED board tightly contacts the heat conductive member.

In accordance with this arrangement, since the LED board, the heat conductive member, and the pressing member can be secured to the housing by the use of only the securing mechanism, it is possible to decrease a number of components. In addition, since the long side edge part of the LED board is pressed by the pressing member in order to secure the LED board, it is possible to tightly attach the LED board to the heat conductive member easily and reliably, which makes it possible to improve heat dissipating efficiency. Furthermore, since the convex part of the positioning mechanism fits into the concave part of the positioning mechanism in a state that the LED board, the heat conductive member, and the pressing member are secured by the securing mechanism, it is possible to position the LED and the lens part reliably just by securing the pressing member to the housing. In addition, the above-mentioned effect is especially pronounced where the light illuminating device uses a surface mounting type LED as the LED.

Conventionally, a bullet type LED comprises a light emitting element and a bullet-shaped mold part to hold the light emitting element, and the mold part is made of epoxy resin. However, epoxy resin suffers from the problem that it is deteriorated by blue light. In addition, even if the mold part is made of polycarbonate resin or acrylic resin, these resins suffer from the problem that they are heat-sensitive. As such, one might consider using a silicon that is tolerant of heat; however, since silicon is soft, it cannot be used to form a bullet-shaped mold part that functions as a lens. In addition, there is a surface mounting type LED that uses silicon as a resin to seal the light emitting element. The surface mounting type LED requires a lens arranged separately from the LED, and furthermore, it requires accurate positioning of the LED and the lens. However, with the subject invention, it is possible to position the LED and the lens easily and accurately.

In addition, the light illuminating device in accordance with claim 2 of this invention comprises a lengthy LED board on which multiple LEDs are loaded, a housing that has an accommodating concave part to house the LED board, a heat conductive member that is arranged between a back surface of the LED board and a bottom surface of the accommodating concave part, a pressing member that has multiple through bores corresponding to each of the multiple LEDs and that presses a long side edge part of the LED board against the bottom surface of the accommodating concave part of the housing, a securing mechanism for securing the LED board, the heat conductive member, and the pressing member to the housing, and a positioning mechanism for positioning the multiple through bores relative to the multiple LEDs, and is characterized by the securing mechanism comprises a first surface that is arranged on either one of the housing or the pressing member and that faces a bottom surface side of the accommodating concave part and a second surface that is arranged on the other of the housing or the pressing member and that makes an abutting contact with the first surface and faces an opening side of the accommodating concave part, the positioning mechanism comprises a convex part that is arranged on either one of the LED board or the pressing member and a concave part that is arranged on the other of the LED board or the pressing member and that fits over the convex part, and each of the multiple through bores is positioned for each of the multiple LEDs, respectively, by making the first surface of the securing mechanism in abutting contact with the second surface of the securing mechanism, and by fittingly inserting the convex part of the positioning mechanism into the concave part of the positioning mechanism in a state that the pressing member presses the long side edge part of the LED board so that the back surface of the LED board tightly contacts the heat conductive member.

In accordance with this arrangement, similar to the invention of the above-mentioned claim 1, since the LED board, the heat conductive member, and the pressing member can be secured to the housing by the use of only the securing mechanism, it is possible to decrease a number of components. In addition, since the long side edge part of the LED board is pressed by the pressing member in order to secure the LED board, it is possible to tightly attach the LED board to the heat conductive member easily and reliably, which makes it possible to improve heat dissipating efficiency. Furthermore, since the convex part of the positioning mechanism fits into the concave part of the positioning mechanism in a state that the LED board, the heat conductive member, and the pressing member are secured by the securing mechanism, it is possible to position the LED and the through bore reliably just by securing the pressing member to the housing. As a result, this arrangement can be preferably applied to bullet-shaped type LEDs.

In order to make it possible to reduce a number of manufacturing processes and to be preferably used for the line light illuminating device, it is preferable that the housing is formed by a drawing process or an extrusion process.

If on both outside side surfaces of the housing a mounting concave part is arranged which makes it possible to mount a diffusing plate that diffuses the light from the LED or an optical filter that selects and transmits only a predetermined wavelength by being engaged with a mounting protrusions arranged on the diffusing plate or the optical filter, it is possible to mount the diffusing plate or the optical filter on the housing easily.

In order to improve a freedom in mounting the light illuminating device, it is preferable that an electric cable for supplying multiple LEDs with electric power extends outside from a corner of the housing.

Effect of the Invention

In accordance with this invention, it is possible to improve the heat dissipation efficiency by reliably keeping the LED board and the heat conductive member in close contact and by reliably positioning the LED and the optical element, such as the lens part, arranged in the housing with a simple arrangement and fewer components.

BEST MODES OF EMBODYING THE INVENTION

Figure 1:
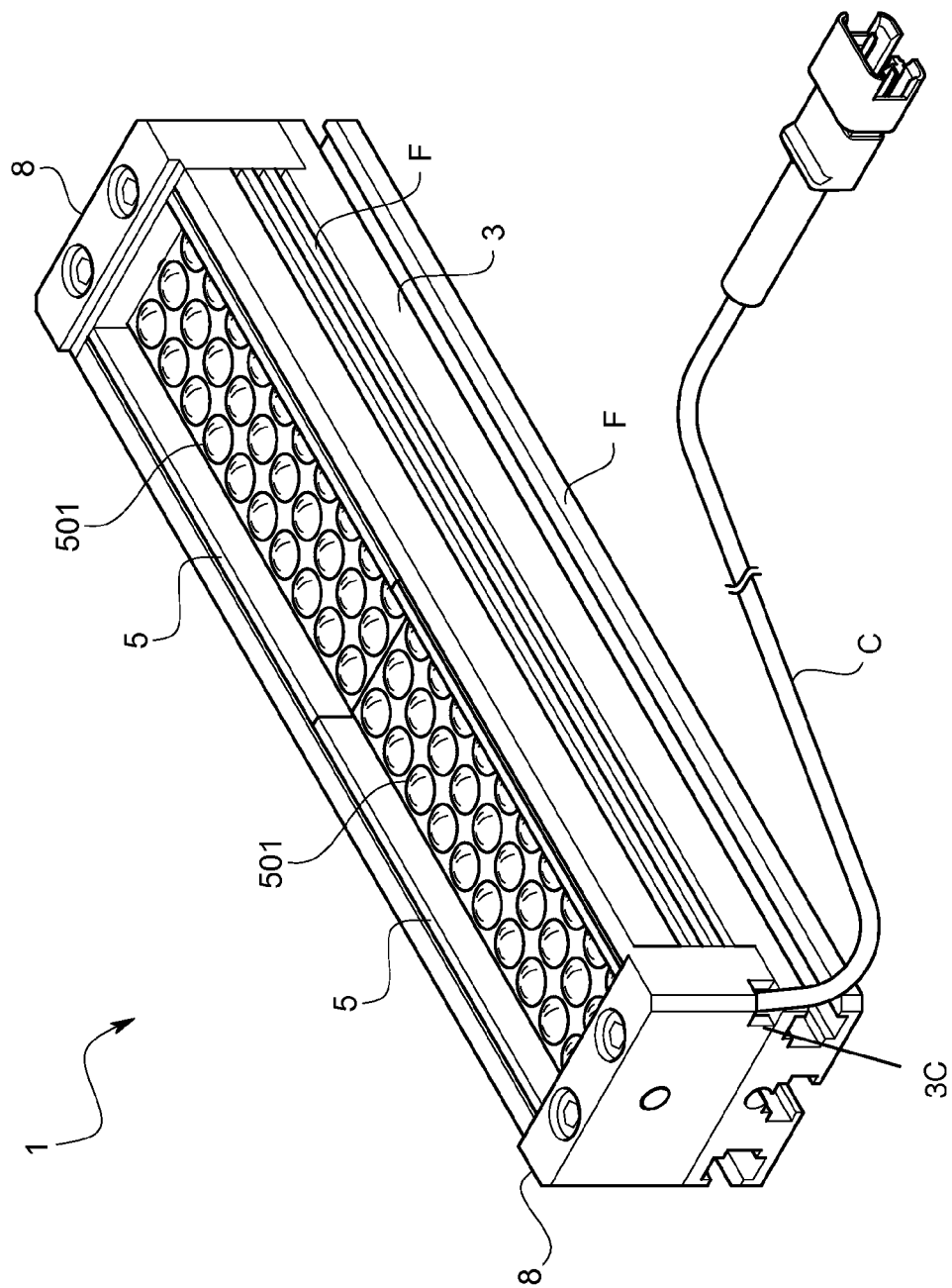
FIG. 1 is a perspective view of a light illuminating device in accordance with one embodiment of this invention.
Figure 3:
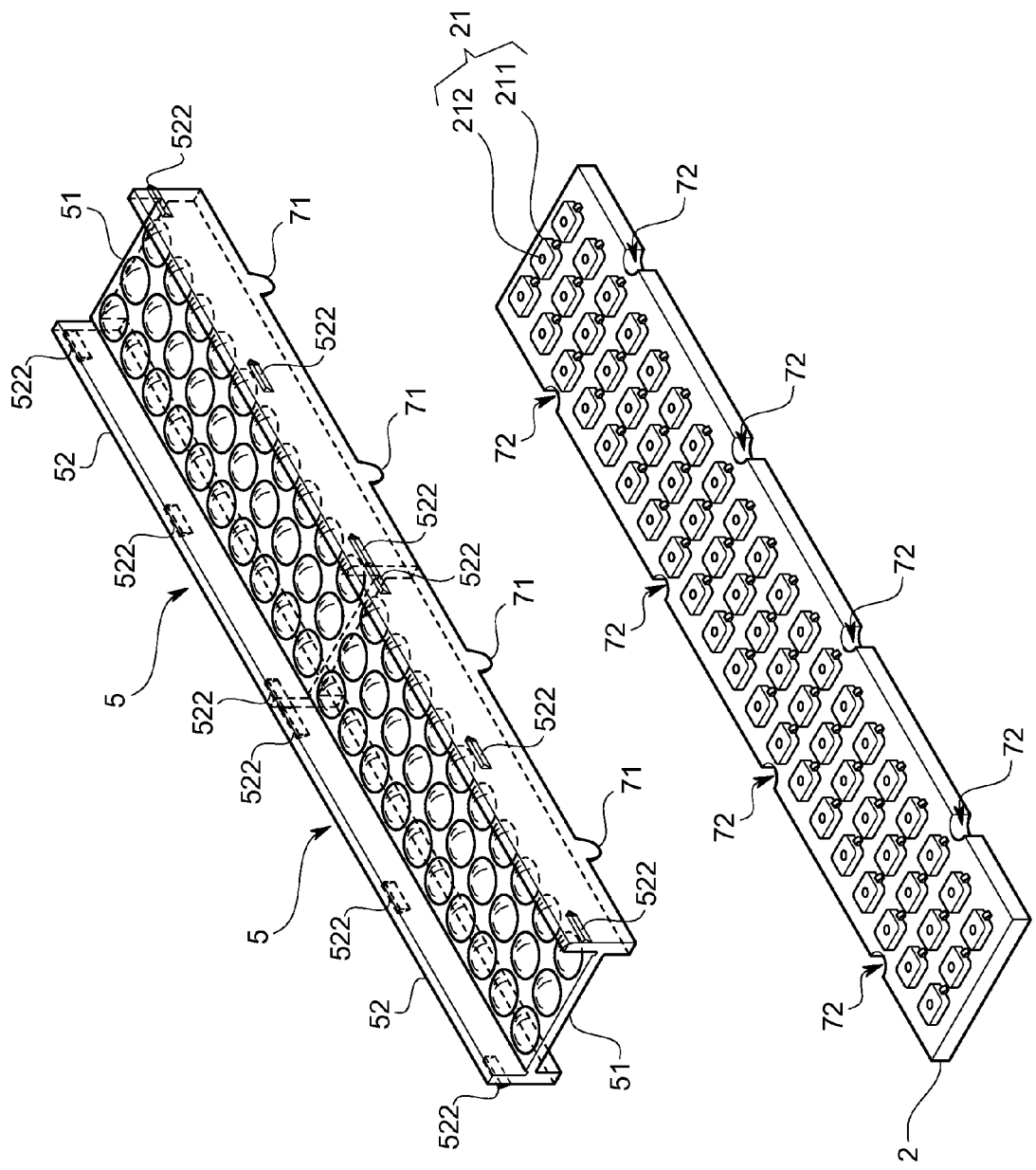
FIG. 3 is a view showing a pressing member, an LED board and a positioning mechanism of this embodiment.
Figure 4:
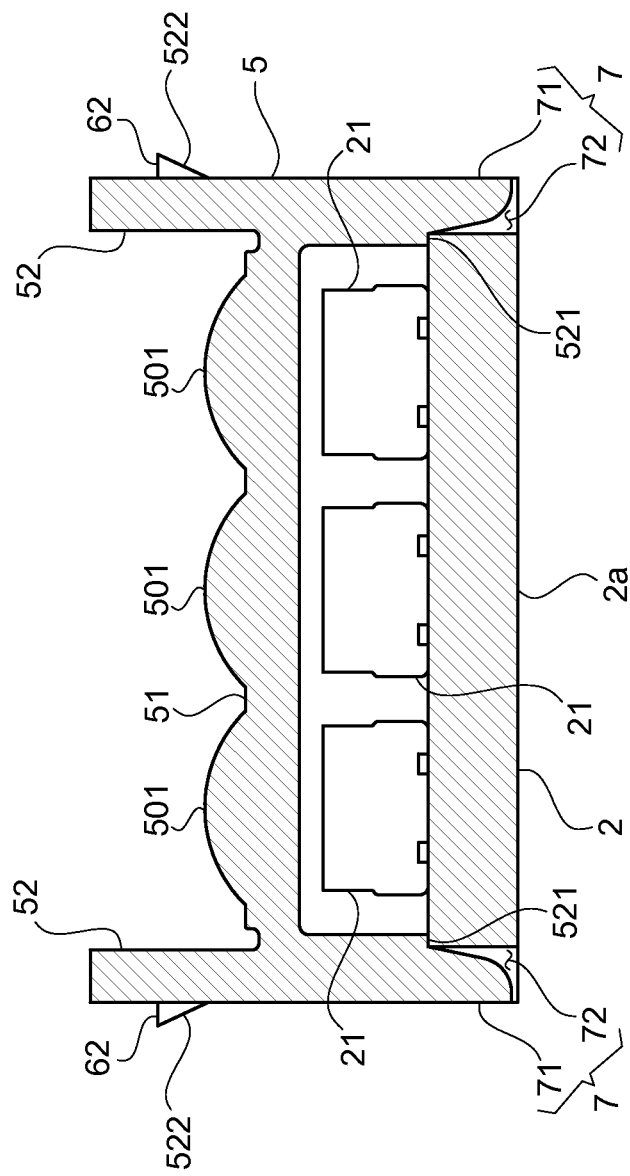
FIG. 4 is a cross-sectional view showing mainly the positioning mechanism.
Figure 5:
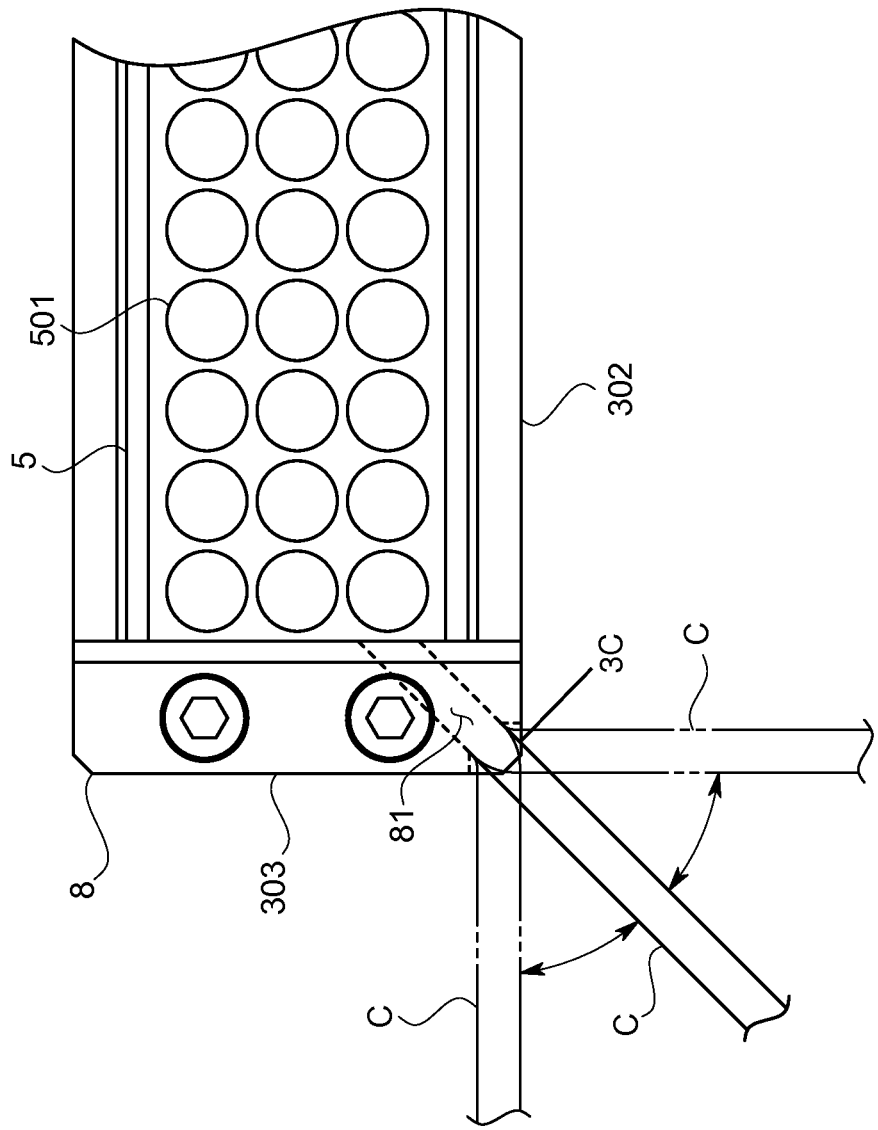
FIG. 5 is a view showing an extending part of an electric cable of this embodiment.
Figure 6:
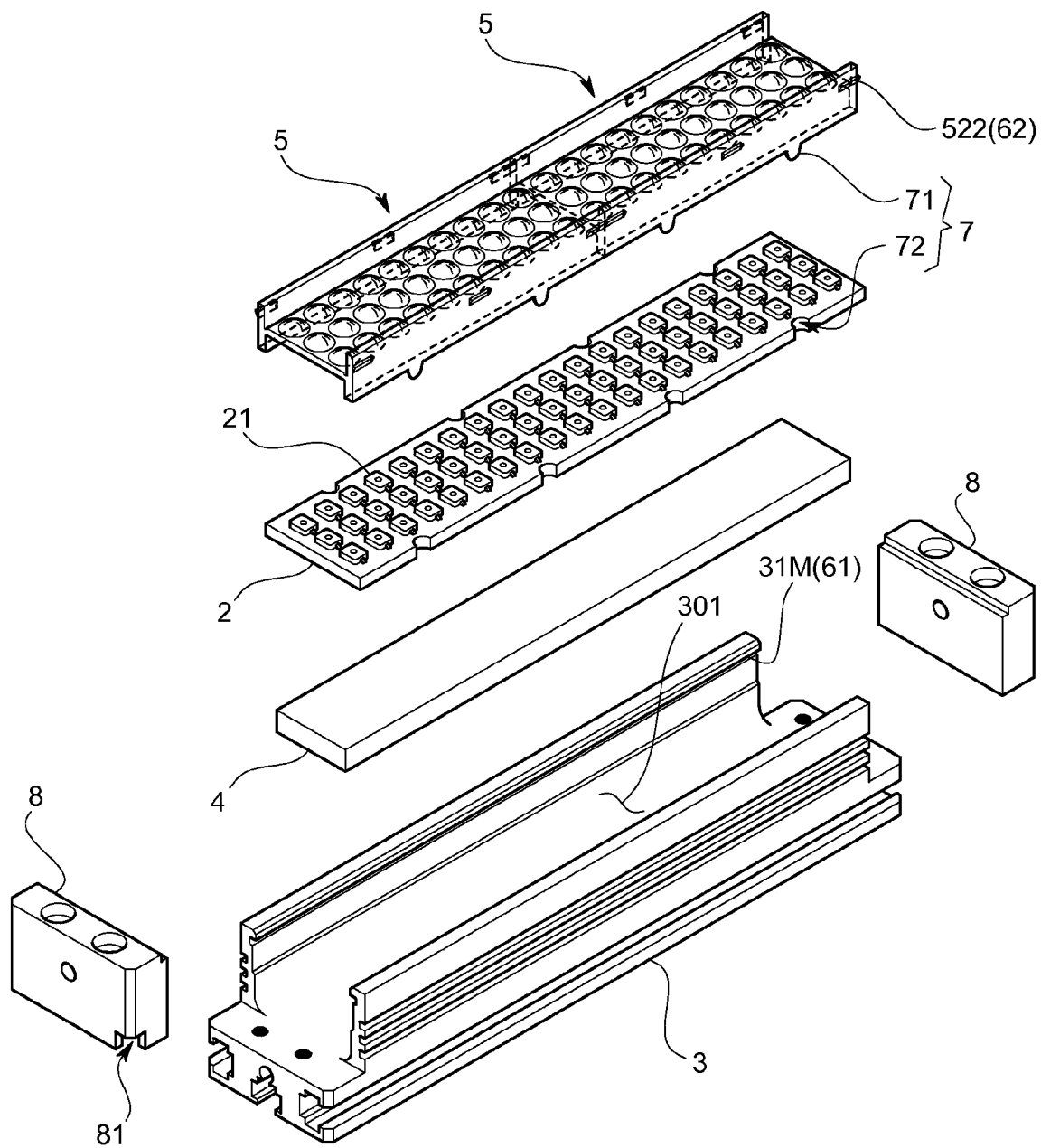
FIG. 6 is an exploded perspective view of the light illuminating device of this embodiment.

Next, one embodiment of light illuminating device 1 in accordance with this invention will be explained with reference to drawings. FIG. 1 is a perspective view showing the light illuminating device 1 of this embodiment, FIG. 2 is a cross-sectional view of the light illuminating device 1, FIG. 3 is an exploded perspective view showing an LED board 2, a pressing member 5 and a positioning mechanism 7, FIG. 4 is a cross-sectional view showing the positioning mechanism 7, FIG. 5 is a view showing an extending part of an electric cable C of a housing 3, and FIG. 6 is an exploded perspective view of the light illuminating device 1.

Device Configuration

The light illuminating device 1 irradiates linear light on a predetermined irradiation area of, for example, a test material (a workpiece), and is used for a product inspection system, or the like, that conducts automatic surface inspection to determine whether there is a flaw or not on a surface of the test material by taking an image of the predetermined irradiation area with an imaging device (not shown in drawings) and by loading the obtained image data with an image processing device (not shown in drawings).

Figure 2:
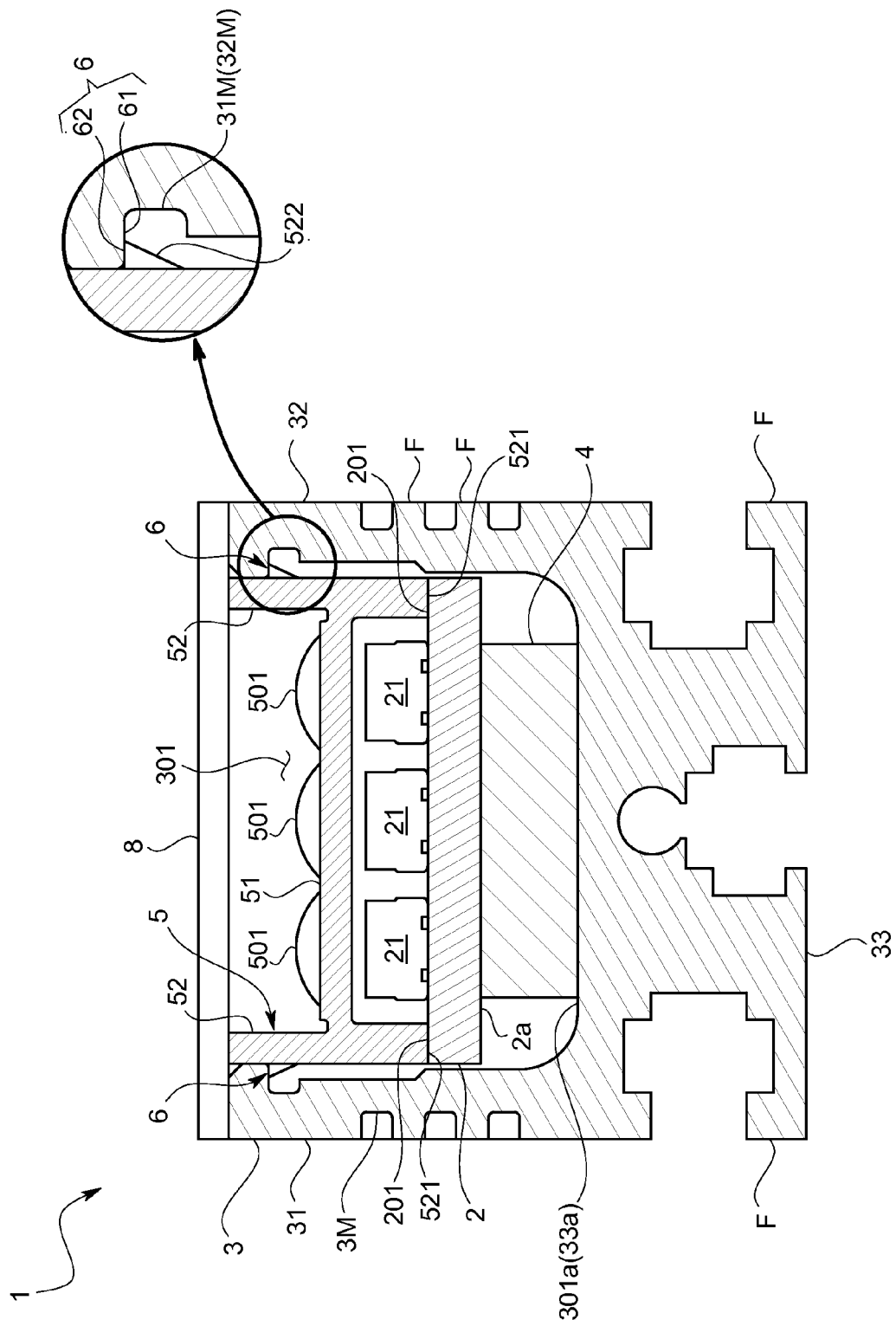
FIG. 2 is a cross-sectional view of this embodiment.

Concretely, the light illuminating device 1 comprises, as shown in FIG. 1 and FIG. 2, the LED board 2, the housing 3, a heat conductive member 4 and the pressing member 5.

The LED board 2 is, as shown in FIG. 3, a lengthy board loaded with multiple LEDs 21. Concretely, the LED board 2 is arranged so that multiple LEDs 21 are mechanically mounted on a surface of a lengthy printed circuit board so as to arranged in a straight line along a length direction with an optical axis of each LED generally aligned in a predetermined direction, and arranged in one row or multiple rows (three rows in FIG. 3) in a width direction. The LED 21 is of a surface mounting type where an LED element 212 is arranged on a center of a package 211 whose shape is, for example, a thin rectangular plate. The LED 21 is so arranged that the LED elements 212 are arranged at a predetermined interval in the long side direction and the short side direction respectively.

The housing 3 has, as shown in FIG. 2, an accommodating concave part 301 that houses the LED board 2, the heat conductive member 4 and the pressing member 5. Concretely, the housing 3 is made of an elongate metal whose cross sectional view orthogonal to a longitudinal direction (an elongate direction) is a general channel shape, and the accommodating concave part 301 is formed by the right and left side walls 31, 32 and the bottom wall 33. In addition, the housing 3 is of an integrated body formed by means of extrusion or drawing, and multiple grooves 3M extending in a longitudinal direction are arranged on an outer surfaces of the right and left walls 31, 32 and an outer surface of the bottom wall 33, and a convexity formed between the grooves 3M functions as a radiating fin F.

The heat conductive member 4 is arranged, as shown in FIG. 2, between a back surface 2a of the LED board 2 and a bottom surface 301a (concretely, an inner surface 33a of the bottom wall 33) of the accommodating concave part 301, and transmits the heat generated on the LED board 2 to the housing 3. The heat conductive member 4 is a band-shaped flat plate having a width generally the same as or a little thinner than that of the LED board 2, made of a material, such as silicon, having predetermined viscoelasticity and insulating properties. In a condition where the LED board 2 is pressed, the heat conductive member 4 is transformed to become dented due to a component, such as a resistor, arranged on a back side of the LED board 2, and ideally makes surface-to-surface contact with the back surface 2a of the LED board 2 and improves thermal conductance efficiency from the LED 21 to the bottom wall 33 of the housing 3.

The pressing member 5 has, as shown in FIGS. 2, 3 and 4, multiple lens parts 501 corresponding to each of the multiple LEDs 21, and pushes the long side edge part 201 of the LED board 2 toward the bottom surface 301a of the accommodating concave part 301. In this embodiment, two pressing members 5 are continuously arranged in series to secure one piece of the LED board 2 to the accommodating concave part 301.

Concretely, the pressing member 5 is of a general "H" character shape in a cross sectional view, orthogonal to a longitudinal direction, and comprises a lens formed part 51 where the lens parts 501 are formed, and flange parts 52 that are formed on both ends of the long side of the lens formed part 51 and are orthogonal to the lens formed part 51. The flange parts 52 are arranged to face the left and right side walls 31 and 32 of the housing 3 when the pressing member 5 is housed in the accommodating concave part 301. Then, generally, the whole surfaces of bottom end surfaces 521 of the flange parts 52 make contact with the long side edge parts 201 of the LED board 2, more specifically, upper surfaces located outside of the LEDs 21 of the LED board 2. With this arrangement, generally uniform force is applied to the long side edge parts 201 of the LED board 2 so that it is possible to prevent the LED board 2 from being warped in a longitudinal direction. In addition, in a state that the bottom end surfaces 521 of the flange parts 52 make contact with the long side edge parts 201 of the LED board 2, the flange parts 52 are set so that generally all of the light irradiated from the LEDs 21 passes through the lens parts 501.

The light illuminating device 1 of this embodiment comprises the securing mechanism 6 to secure the LED board 2, the heat conductive member 4 and the pressing member 5 to the housing 3, and the positioning mechanism 7 to position the multiple lens parts 501 relative to the multiple LEDs 21.

Next, the securing mechanism 6 and the positioning mechanism 7 will be explained.

The securing mechanism 6, as shown in a partially enlarged view of FIG. 2, comprises a first surface 61 that is arranged on either one of the housing 3 and the pressing member 5 and faces the bottom surface 301a side of the accommodating concave part 301, and a second surface 62 that is arranged on the other of the housing 3 and the pressing member 5 and that makes an abutting contact with the first surface 61 and faces an opening side of the accommodating concave part 301.

The first surface 61 is formed by a surface (a downward facing surface), facing the bottom surface 301a side of the accommodating concave part 301, of the concave grooves 31M and 32M, arranged on the left and right side walls 31 and 32, respectively, of the housing 3 and extend in a longitudinal direction. The second surface 62 is formed by a surface (an upward facing surface), facing an open side of the accommodating concave part 301, of an engaging projection 522 arranged on an outer side surface of the flange part 52. Multiple (three in FIG. 3) engaging projections 522 are arranged at even intervals on the outside surfaces of the flange parts 52. The shape of the engaging projection 522 is a general right-angle triangle in a cross-section, comprising a surface (forming the second surface 62), orthogonal to the direction of insertion of the pressing member 5, and an inclined surface that is continuous to the surface and that faces the direction of insertion of the pressing member 5.

In a state that the back surface 2a of the LED board 2 is tightly attached to the heat conductive member 4 and the heat conductive member 4 is tightly attached to the bottom surface 301a of the accommodating concave part 301 by pressing the pressing member 5 against the long side edge part 201 of the LED board 2, the engaging projections 522 fit into the concave grooves 31M and 32M, and the first surfaces 61 make abutting contact with the second surfaces 62.

The positioning mechanism 7 comprises, as shown in FIG. 3 and FIG. 4, convex parts 71 arranged on either one of the LED board 2 and the pressing member 5 and concave parts 72 arranged on the other of the LED board 2, and the pressing member 5 and that fits over the convex parts 71.

One or a plurality of convex parts 71 (two, in FIG. 3 and FIG. 4) are arranged on the bottom end surface 521 of both of the flange parts 52 of the pressing member 5. Each of convex parts 71 is tapered and its cross-sectional view (orthogonal to the longitudinal direction) is generally a semicircle. In addition, one or a plurality of concave parts 72 are formed on the long side edge parts 201 of the LED board 2 corresponding to the convex parts 71. Each of concave parts 72 is inwardly concave from a side surface of the LED board 2, and its plan view is a generally a semicircle.

Each center axis of the multiple lens parts 501 coincides with each optical axis of the multiple LEDs 21 by fittingly inserting the concave parts 72 over the convex parts 71, in a state that the first surface 61 makes an abutting contact with the second surface 62 of the securing mechanism 6. Concretely, the LEDs 21 and the lens parts 501 are positioned by fittingly inserting a proximal end part of the convex parts 71 into openings of the concave parts 72 on a board surface side. At this time, since multiple numbers of the convex parts 71 and concave parts 72 are arranged in the long side direction and in the short side direction, it is possible to position the LEDs 21 and the lens parts 501 in the long side direction and in the short side direction.

Furthermore, in the light illuminating device 1 of this embodiment, as shown in FIGS. 1 and 5, an electric cable C for supplying the multiple LEDs 21 with electric power extends from a corner 3C of the housing 3 to the outside. In other words, as shown in FIG. 5, the electric cable C extends from the corner 3C formed by a long side surface 302 and a short side surface 303. Then it is so arranged that the electric cable C can be transformed in a direction along the longitudinal direction or in a direction along the short side direction or rotated. Concretely, the electric cable C extends from the housing 3 to outside by means of a guide groove 81 arranged on a block body 8, which shape is generally cuboid, and is secured to a longitudinal end part of the housing 3, and can be transformed in the longitudinal direction or in the short side direction or rotated. The guide groove 81 extends toward the corner part of the block body 8 and is formed to be wider as it approaches the corner part of the block body 8.

Concretely, for the two surfaces (the long side surface 302 and the short side surface 303) forming the corner, in a case of extending the cable C from the short side surface 303, this embodiment adopts an arrangement to locate the electric cable C inside (the housing 3 side) of the long side surface 302 so that the outer circumferential surface of the electric cable C and the long side surface 302 become aligned. Meanwhile, in a case of extending the cable C from the long side surface 302, this embodiment adopts an arrangement to locate the electric cable C inside (the housing 3 side) of the short side surface 303 so that the outer circumferential surface of the electric cable C and the short side surface 303 become aligned. With this arrangement, a degree of freedom in mounting this light illuminating device 1 is improved.

Next, a process of assembling the light illuminating device 1 having this arrangement will be explained with reference to the drawings.

First, the heat conductive member 4 is placed in the accommodating concave part 301 of the housing 3 that is formed by a drawing process or an extrusion process and with which a predetermined process is provided to secure the block bodies 8 at both end parts of the housing 3, and then the LED board 2 is placed on top of the heat conductive member 4.

Next, the pressing member 5 is inserted into the accommodating concave part 301 from an opening of the accommodating concave part 301 until the engaging projections 522 are fittingly inserted into the concave grooves 31M and 32M. At a time when the engaging projections 522 are fittingly inserted into the concave grooves 31M and 32M, the first surfaces 61 make an abutting contact with the second surfaces 62. At this time, the bottom end surfaces 521 of the flange parts 52 of the pressing member 5 push the long side edge parts 201 of the LED board 2 toward the bottom surface 301a side of the accommodating concave part 301, and then the bottom end surfaces 521 are in a state of being secured to the long side edge parts 201.

In addition, at this time when the pressing member 5 is secured to the LED board 2, the convex parts 71 arranged on the bottom end surfaces 521 of the flange parts 52 fit into the concave parts 72 arranged on the LED board 2 so that the LEDs 21 and the lens parts 501 are positioned in a plane direction. As mentioned, it is possible not only to secure the LED board 2, the heat conductive member 4, and the pressing member 5 to the housing 3, but also to position the LEDs 21 and the lens parts 501 by fittingly inserting the engaging projections 522 into the concave grooves 31M and 32M.

Later, the block bodies 8 are threadably secured to both end parts of the housing 3. At this time, the guide groove 81 for extending the electric cable C from the corner of the housing 3 is formed for the block body 8, which is secured to the end part side where the electric cable C (not shown in FIG. 6) extends.

Effect of this Embodiment

In accordance with the light illuminating device 1 of this embodiment, since it is possible to secure the LED board 2, the heat conductive member 4, and the pressing member 5 to the housing 3 by the use of one securing mechanism 6 alone, a number of components can be reduced. In addition, since the long side edge part 201 of the LED board 2 is pushed by the pressing member 5 so as to secure the LED board 2, there is no chance that the LED board 2 warps in a longitudinal direction. As a result, since it is possible to tightly contact the LED board 2 to the heat conductive member 4 easily and reliably, the heat dissipation efficiency can be improved. Furthermore, since the convex parts 71 of the positioning mechanism 7 fit into the concave parts 72 at the same time when the LED board 2, the heat conductive member 4, and the pressing member 5 are secured by means of the securing mechanism 6, it is possible to position the LEDs 21 and the lens parts 501 easily and reliably.

Other Modified Embodiment

The present invention is not limited to the above-mentioned embodiment. In the following explanation, the same parts as those in the above-mentioned embodiment are denoted by the same reference numerals as in those embodiments.

Figure 7:
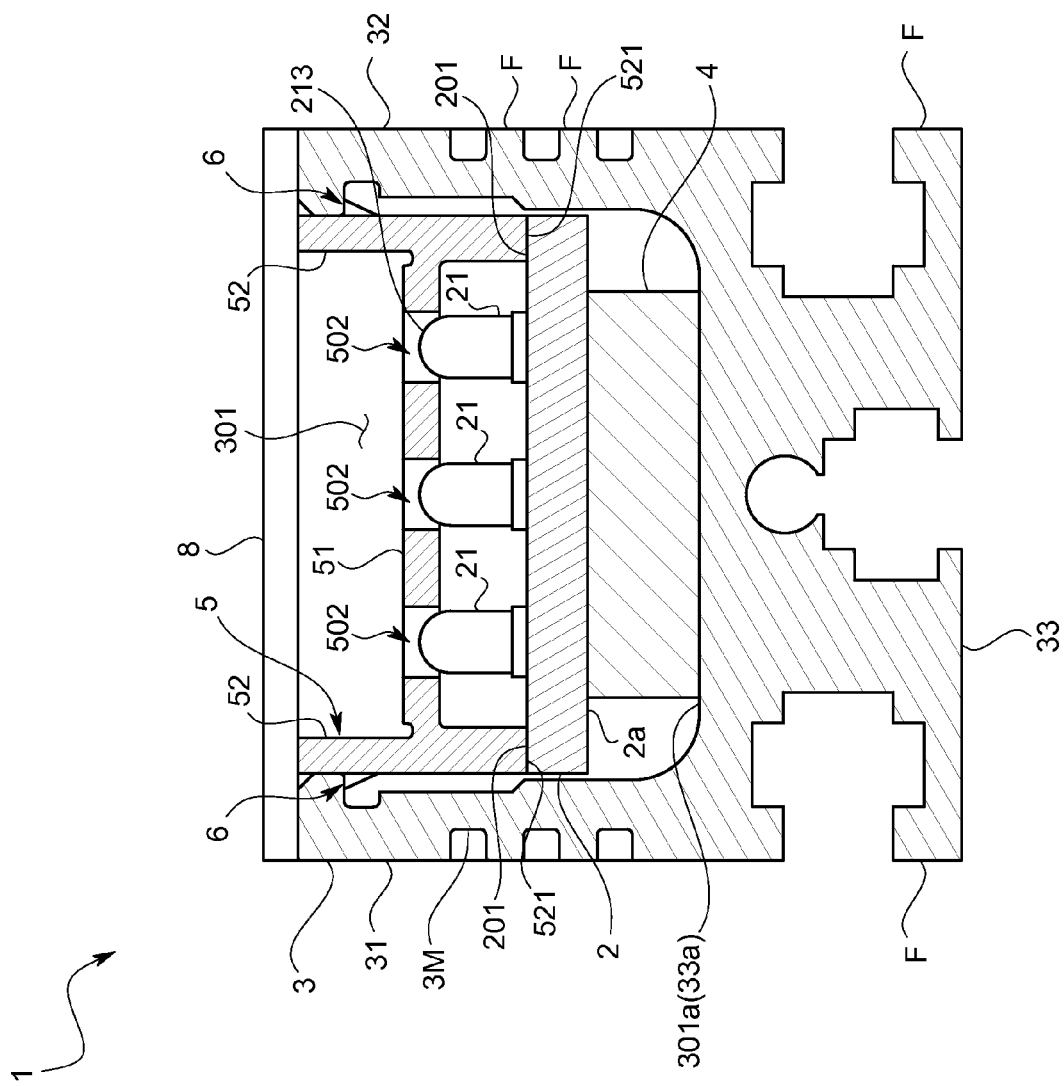
FIG. 7 is a cross-sectional view of a light illuminating device in accordance with another modified embodiment.

For example, the pressing member 5 in the above-mentioned embodiment comprises multiple lens parts 501; however, in a case that the LEDs 21 loaded on the LED board 2 are bullet shaped, as shown in FIG. 7, the pressing member 5 may have through bores 502 arranged to correspond to each of the multiple LEDs 21. With this arrangement, a mold part 213 of the bullet shaped LED 21 can have an arrangement of being able to be inserted into the through bore 502 so that it is possible to directly irradiate the light irradiated from the mold part 213 to the outside. Even for a case of a surface mounting type LEDs 21, it is possible to irradiate the light irradiated from the surface mounting type LEDs 21 to the outside.

Figure 8:
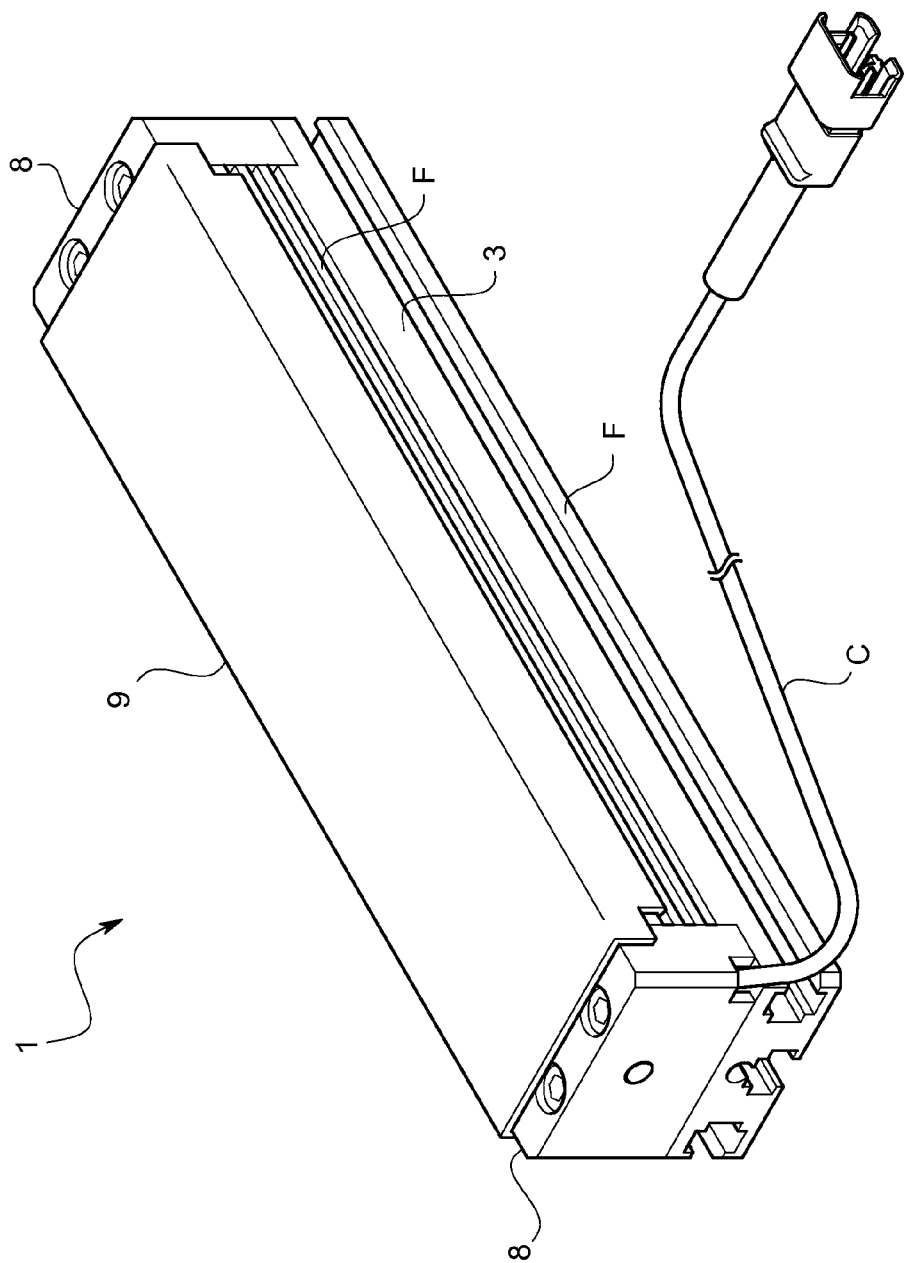
FIG. 8 is a perspective view of the light illuminating device of the other modified embodiment.
Figure 9:
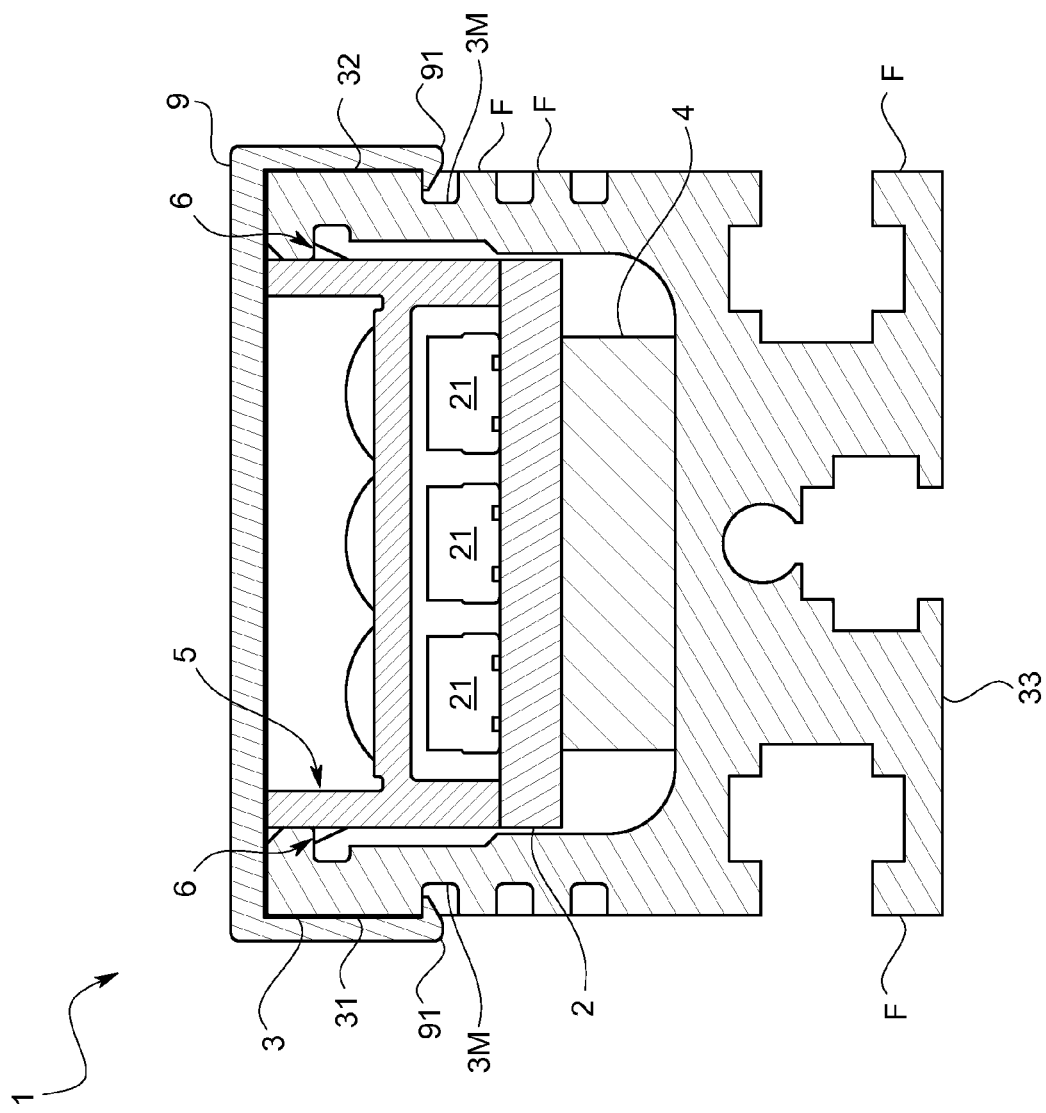
FIG. 9 is a cross-sectional view of the light illuminating device of the other modified embodiment.

In addition, the light illuminating device 1 of the above-mentioned embodiment may comprise a diffusing plate for diffusing the light from the LEDs 21 or an optical filter that selects and transmits only the light having a predetermined wavelength. FIG. 8 shows a perspective view of a light illuminating device having a diffusing plate, and FIG. 9 shows a cross-sectional view of the light illuminating device. The diffusing plate 9 is of a general channel shape in a cross-sectional view, and is provided with mounting protrusions 91 formed on each facing wall of the diffusing plate 9. The diffusing plate 9 can be mounted by engaging the mounting protrusions 91 with grooves 3M (mounting concave part) arranged on outside surfaces of the housing 3. With this arrangement, it is possible to eliminate the use of a securing screw in a case of mounting the diffusing plate 9, thereby reducing a number of components.

Furthermore, a length of the light illuminating device may be changed by changing a number of the LED boards and a number of the pressing members arranged in series.

In addition, if multiple pressing members are prepared having lens parts whose curvature varies, it is possible to change the curvature of the lens part simply by changing the pressing member to be secured to the housing. As result, it is possible to manufacture a light illuminating device having directional characteristics in accordance with various objects.

In addition, a part or all of the above-mentioned embodiment or the modified embodiment may be appropriately combined, and it is a matter of course that the present invention is not limited to the above-mentioned embodiment and may be variously modified without departing from the spirit of the invention.

INDUSTRIAL APPLICABILITY

With a simple arrangement having a fewer number of components, it is possible to provide a light illuminating device that can improve the heat dissipating efficiency and, furthermore, that can position the LEDs and the optical elements, such as the lens parts arranged on the housing, reliably.

EXPLANATION OF CODES

1 . . . light illuminating device
2 . . . LED board
21 . . . LED
201 . . . long side edge part
2a . . . back surface of LED board
3 . . . housing
301 . . . accommodating concave part
301a . . . bottom surface of accommodating concave part
4 . . . heat conductive member
5 . . . pressing member
501 . . . lens part
502 . . . through bore
6 . . . securing mechanism
61 first surface
62 second surface
7 . . . positioning mechanism
71 . . . convex part
72 . . . concave part
C . . . electric cable
9 . . . diffusing plate
91 . . . mounting protrusion

The invention claimed is:

1. A light illuminating device comprising
a lengthy LED board on which multiple LEDs are loaded,
a housing that has an accommodating concave part to house the LED board,
a heat conductive member that is arranged between a back surface of the LED board and a bottom surface of the accommodating concave part,
a pressing member that has multiple lens parts corresponding to each of the multiple LEDs and that presses a long side edge part of the LED board against the bottom surface of the accommodating concave part of the housing,
a securing mechanism for securing the LED board, the heat conductive member and the pressing member to the housing, and
a positioning mechanism for positioning the multiple lens parts relative to the multiple LEDs, wherein
the securing mechanism comprises a first surface that is arranged on either one of the housing and the pressing member and that faces a bottom surface side of the accommodating concave part and a second surface that is arranged on the other of the housing and the pressing member and that makes an abutting contact with the first surface and faces an opening side of the accommodating concave part,
the positioning mechanism comprises a convex part that is arranged on either one of the LED board and the pressing member and a concave part that is arranged on the other of the LED board and the pressing member and that fits over the convex part, and
each of the multiple lens parts is positioned for each of the multiple LEDs respectively by making the first surface of the securing mechanism an abutting contact with the second surface of the securing mechanism and by fittingly inserting the convex part of the positioning mechanism into the concave part of the positioning mechanism in a state that the pressing member presses the long side edge part of the LED board so that the back surface of the LED board tightly contacts the heat conductive member.

2. The light illuminating device described in claim 1, wherein
the housing is formed by a drawing process or an extrusion process.

3. The light illuminating device described in claim 1, wherein
on both outside side surfaces of the housing is a mounting concave part that makes it possible to mount a diffusing plate, which diffuses the light from the LED or an optical filter that selects and transmits only a predetermined wavelength, by being engaged with a mounting protrusion arranged on the diffusing plate or the optical filter.

4. The light illuminating device described in claim 1, wherein
an electric cable for supplying multiple LEDs with electric power extends outside from a corner of the housing.

* * * * *